United States Patent
Yang et al.

(10) Patent No.: US 10,683,247 B1
(45) Date of Patent: Jun. 16, 2020

(54) CATALYSTS AND INTEGRATED PROCESSES FOR PRODUCING TRIFLUOROIODOMETHANE

(71) Applicant: Honeywell International Inc., Morris Plains, NJ (US)

(72) Inventors: Terris Yang, East Amherst, NY (US); Haiyou Wang, Amherst, NY (US); Yuon Chiu, Denville, NJ (US); Richard Wilcox, West Caldwell, NJ (US); Christian Jungong, Depew, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 16/702,225

(22) Filed: Dec. 3, 2019

Related U.S. Application Data

(60) Provisional application No. 62/783,412, filed on Dec. 21, 2018.

(51) Int. Cl.
*C07C 17/093* (2006.01)
*C07C 19/16* (2006.01)
*B01J 27/224* (2006.01)

(52) U.S. Cl.
CPC ........... *C07C 17/093* (2013.01); *B01J 27/224* (2013.01); *C07C 19/16* (2013.01); *C07C 2527/22* (2013.01)

(58) Field of Classification Search
CPC ..... C07C 17/093; C07C 17/361; C07C 19/16; C07C 17/158; C07C 19/07; B01J 27/224
See application file for complete search history.

(56) References Cited

U.S. PATENT DOCUMENTS

| | | |
|---|---|---|
| 7,071,367 B1 | 7/2006 | Mukhopadhyay et al. |
| 7,132,578 B1 | 11/2006 | Mukhopadhyay et al. |
| 7,196,236 B2 | 3/2007 | Mukhopadhyay et al. |
| 8,034,985 B2 | 10/2011 | Yang et al. |
| 8,722,945 B2 | 5/2014 | Yang et al. |
| 8,871,986 B2 | 10/2014 | Yang et al. |
| 2008/0200735 A1 | 8/2008 | Yang et al. |
| 2009/0137852 A1 | 5/2009 | Yang et al. |

FOREIGN PATENT DOCUMENTS

| | | |
|---|---|---|
| CN | 102464569 B | 5/2012 |
| CN | 102992943 A | 3/2013 |

OTHER PUBLICATIONS

Lee, K.-H. et al. (2001). Synthesis of CF3I by Direct Iodination of CF3COOH on Solid Catalyst. Hwahak Konghak, 39 (2):144-149, in Korean with an English abstract.

*Primary Examiner* — Jafar F Parsa
(74) *Attorney, Agent, or Firm* — Faegre Drinker Biddle & Ream LLP

(57) ABSTRACT

The present disclosure provides a process for producing trifluoroiodomethane ($CF_3I$). The process may include providing a vapor-phase reactant stream comprising trifluoroacetic acid and iodine and reacting the reactant stream in the presence of a catalyst to produce a product stream comprising the trifluoroiodomethane. The catalyst includes silicon carbide.

20 Claims, 1 Drawing Sheet

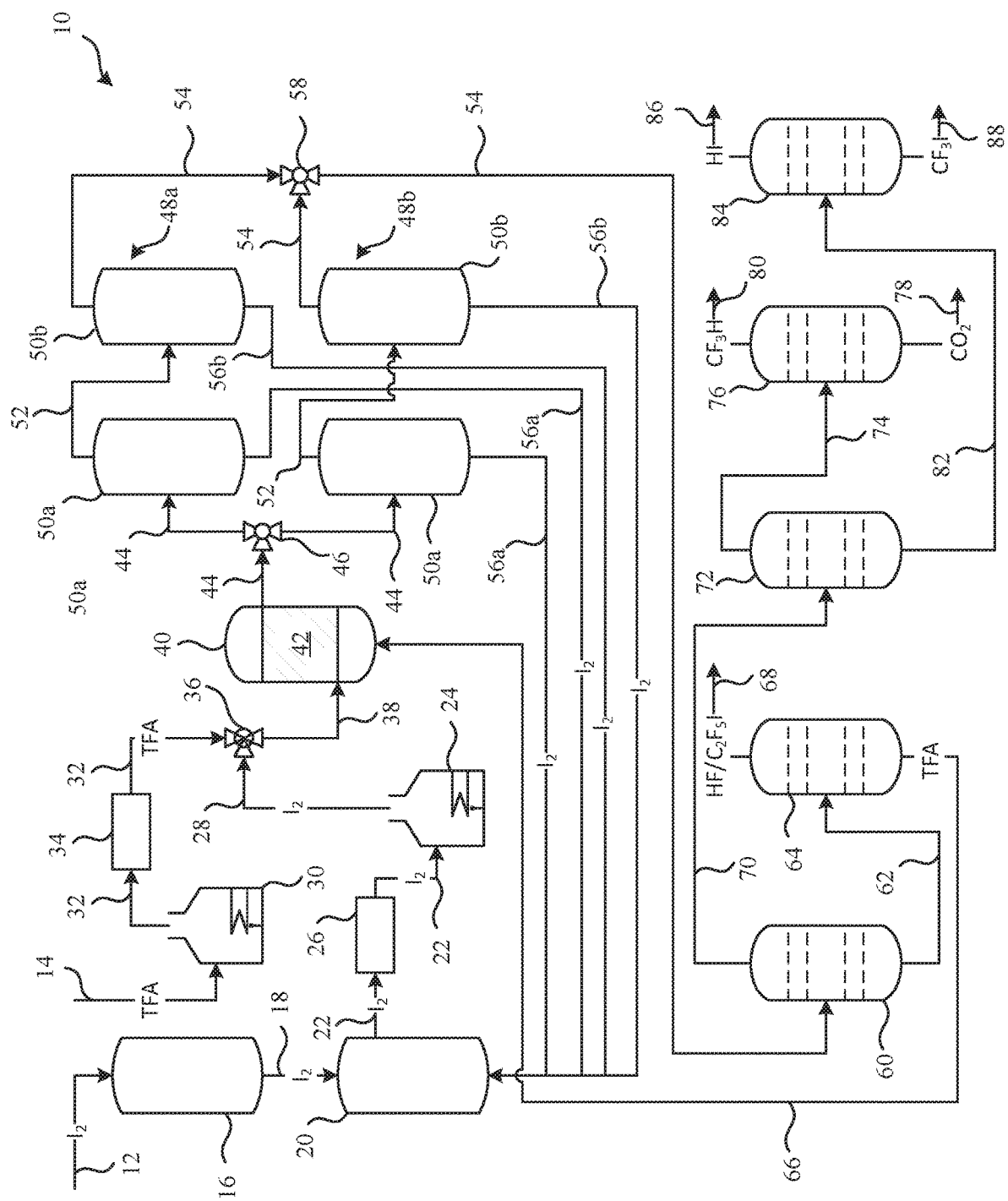

CATALYSTS AND INTEGRATED PROCESSES FOR PRODUCING TRIFLUOROIODOMETHANE

CROSS-REFERENCE TO RELATED APPLICATION

This application claims priority to U.S. Provisional Application No. 62/783,412, filed Dec. 21, 2018, which is herein incorporated by reference in its entirety.

FIELD

The present disclosure relates to processes for producing trifluoroiodomethane ($CF_3I$). Specifically, the present disclosure relates to catalysts and integrated processes to produce trifluoroiodomethane.

BACKGROUND

Trifluoroiodomethane ($CF_3I$) is a useful compound in commercial applications, as a refrigerant or a fire suppression agent, for example. Trifluoroiodomethane is an environmentally acceptable compound with a low global warming potential and a low ozone depletion potential. Trifluoroiodomethane can replace more environmentally damaging materials.

Methods of preparing trifluoroiodomethane from trifluoroacetic acid and elemental iodine are known. For example, Kyong-Hwan Lee et al., "Synthesis of $CF_3I$ by Direct Iodination of $CF_3COOH$ on Solid Catalyst," discloses a vapor phase reaction of TFA and $I_2$ to produce $CF_3I$. TFA liquid is metered into a three-necked flask containing iodine and heated to vaporize the iodine. Together, the TFA and iodine vapors flow to a reactor charged with a solid catalyst. The output of the reactor flows into a heated collector, and then through a heated line, to a second collector. The vapor stream including the $CF_3I$ flows through a basic solution to neutralize acids. Thus, Lee discloses a batch process, with a fixed quantity of $I_2$ vaporized together with a fixed quantity of TFA. Lee discloses that catalysts with activated carbon are better than alumina.

U.S. Pat. No. 8,722,945 to Yang et al. discloses a vapor phase reaction of a precursor, such as TFA, with a source of iodine, such as $I_2$, to produce a fluoroiodoalkane, such as $CF_3I$. The process may be a batch process or a continuous process. The patent discloses methods for pretreating a solid catalyst and regenerating the solid catalyst. The solid catalyst may include an alkali metal, an alkaline earth metal, transition metals, lanthanides or rare earth metals, including various metal salts. The solid catalyst may be supported on an activated carbon substrate.

U.S. Pat. No. 8,8871,986 to Yang et al. discloses a vapor phase reaction of a precursor, such as TFA, with a source of iodine, such as $I_2$, to produce $CF_3I$. The process may be a batch process or a continuous process. The patent discloses various catalyst promoters to promote catalyst activity and stability. The catalysts include alkaline metals, alkaline earth metals, and salts thereof supported by a carbonaceous carrier. Non-carbonaceous carriers may also be employed.

U.S. Pat. No. 8,034,985 to Yang et al. discloses a vapor phase reaction of a precursor, such as TFA, with a source of iodine, such as $I_2$, to produce a fluoroiodoalkane, such as $CF_3I$. The patent discloses various catalysts including $d^1s^1$ and/or lanthanide elements. The catalysts can be used in bulk or supported by activated carbon. Non-carbonaceous carriers may also be employed.

The above references generally describe the use of activated carbon as a catalyst support. While activated carbon catalysts may afford excellent selectivity to producing $CF_3I$, they are susceptible to rapid deactivation as coke deposits accumulate on the catalyst surface, decreasing the effective surface area of the catalyst. In some cases, oxygen gas is co-fed with the reactants to simultaneously remove the deposits by oxidation. However, the oxygen gas may also lead to progressive reduction in the quantity of carbon in the catalyst as the carbon in the catalyst combusts during the reaction. The loss of carbon may adversely impact the activity of the catalyst.

Thus, there is a need to develop a more durable catalyst along with an efficient process that may be scaled to produce commercial quantities of trifluoroiodomethane.

SUMMARY

The present disclosure provides integrated processes for producing trifluoroiodomethane and a silicon carbide catalyst for producing trifluoroiodomethane.

In one embodiment, the present invention provides a process for producing trifluoroiodomethane ($CF_3I$). The process includes providing a vapor-phase reactant stream comprising trifluoroacetic acid and iodine and reacting the reactant stream in the presence of a catalyst to produce a product stream comprising the trifluoroiodomethane. The catalyst includes silicon carbide.

In another embodiment, the present invention provides a process for producing trifluoroiodomethane ($CF_3I$). The process includes the steps of reacting trifluoroacetic acid and iodine in the vapor phase in the presence of a catalyst to produce a product stream including the trifluoroiodomethane and unreacted iodine, removing at least some of the unreacted iodine from the product stream by cooling the product stream to form solid iodine, producing liquid iodine from the solid iodine, and recycling the liquified iodine to the reacting step. The solid iodine may form in one of a first iodine removal vessel or a second iodine removal vessel. The liquid iodine may be produced by heating the first iodine removal vessel to liquefy the solid iodine when cooling the product stream through the second iodine removal vessel, or by heating the second iodine removal vessels to liquefy the solid iodine when cooling the product stream through the first iodine removal vessel. The catalyst includes silicon carbide.

The above mentioned and other features of the disclosure, and the manner of attaining them, will become more apparent and will be better understood by reference to the following description of embodiments taken in conjunction with the accompanying drawings.

BRIEF DESCRIPTION OF THE DRAWINGS

The FIGURE is a process flow diagram showing an integrated process for manufacturing trifluoroiodomethane.

DETAILED DESCRIPTION

The present disclosure provides integrated processes for the manufacture of trifluoroiodomethane ($CF_3I$) from trifluoroacetic acid (TFA) and iodine ($I_2$) that include the use of a silicon carbide based catalyst. It has been found that use of the silicon carbide based catalyst may provide for the efficient manufacture of trifluoroiodomethane on a commercial scale. The efficiency of the manufacture of trifluoroiodomethane is further enhanced by the recycling the reactants. However, recycling iodine presents challenges because it is solid below 113.7° C. The present disclosure also provides integrated processes for the manufacture of trifluoroiodomethane that include recycling of iodine in an efficient and continuous manner.

Catalysts including silicon carbide have been found to provide useful alternative to catalysts including activated carbon. Compared to activated carbon catalysts, silicon carbide catalysts are more resistant to oxidation, more thermally stable, more chemically inert, and less susceptible to deactivation. Silicon carbide catalysts may be in the form of beads, pellets, extrudates, powder, spheres, or mesh, for example. Silicon carbide exists in two main forms: alpha silicon carbide and beta silicon carbide. Either form may be used, but the beta silicon carbide is preferred because it has a larger surface area per unit weight.

As disclosed herein, the trifluoroiodomethane is produced from a reactant stream comprising trifluoroacetic acid (TFA) and iodine ($I_2$). The TFA and iodine are anhydrous. It is preferred that there be as little water in the reactant stream as possible because any water in the reactant stream may favor secondary reaction pathways resulting in the formation of undesired byproducts, such as trifluoromethane ($CF_3H$).

The TFA is substantially free of water, including water by weight in an amount less than about 1,000 parts per million (ppm), about 500 ppm, about 300 ppm, about 200 ppm, about 100 ppm, about 50 ppm, about 30 ppm, about 20 ppm, or about 10 ppm, or less than any value defined between any two of the foregoing values. Preferably, the TFA comprises water by weight in an amount less than about 100 ppm. More preferably, the TFA comprises water by weight in an amount less than about 30 ppm. Most preferably, the TFA comprises water by weight in an amount less than about 10 ppm.

The iodine is substantially free of water, including by weight in an amount less than about 500 ppm, about 300 ppm, about 200 ppm, about 100 ppm, about 50 ppm, about 30 ppm, about 20 ppm, or about 10 ppm, or less than any value defined between any two of the foregoing values. Preferably, the iodine comprises water by weight in an amount less than about 100 ppm. More preferably, the iodine comprises water by weight in an amount less than about 30 ppm. Most preferably, the iodine comprises water by weight in an amount less than about 10 ppm.

TFA is readily available in commercial quantities from Halocarbon Products Corporation, Peachtree Corners, Ga., or from Solvay S.A., Brussels, Belgium, for example. Solid iodine is commercially available from SQM, Santiago, Chile, or Kanto Natural Gas Development Co., Ltd, Chiba, Japan.

In the reactant stream, a mole ratio of iodine to TFA may be as low as about 0.1:1, about 0.2:1, about 0.3:1, about 0.4:1, about 0.5:1, about 0.6:1, about 0.7:1, about 0.8:1, about 0.9:1, or about 1:1, or as high as about 1.1:1, about 1.2:1, about 1.3:1, about 1.4:1, about 1.5:1, about 1.6:1, about 1.8:1, about 2.0:1, about 2.5:1, about 3.0:1, about 3.5:1, about 4.0:1, about 4.5:1, or about 5.0:1, or within any range defined between any two of the foregoing values, such as about 0.1:1 to about 5.0:1, about 0.5:1 to about 4.5:1, about 1:1 to about 4.0:1, about 1.5:1 to about 3.5:1, about 2.0:1 to about 3.0:1, about 0.9:1 to about 1.1:1, about 0.8:1 to about 1.2:1, about 0.5:1 to about 1.5:1, about 1:1 to about 2:1, about 0.8:1 to about 1.5:1, or about 0.9:1 to about 1.2:1, for example. Preferably, the mole ratio of TFA to iodine is from about 0.8:1 to about 1.5:1. More preferably, the mole ratio of TFA to iodine is from about 1:1 to about 1.2:1. Most preferably, the mole ratio of TFA to iodine is from about 1:1 to about 1.1:1.

The reactant stream may react in the presence of a catalyst contained within a reactor to produce a product stream comprising trifluoroiodomethane and reaction by-products carbon dioxide ($CO_2$) and hydroiodic acid (HI) according to Equation 1 below:

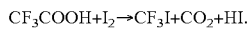

$$CF_3COOH + I_2 \rightarrow CF_3I + CO_2 + HI. \qquad \text{Eq. 1:}$$

The reactor may be a heated tube reactor, such a fixed bed tubular reactor, including a tube containing the catalyst. The tube may be made of a metal such as stainless steel, nickel, and/or a nickel alloy, such as a nickel-molybdenum alloy, a nickel-chromium-molybdenum alloy, or a nickel-copper alloy. The tube reactor is heated, thus also heating the catalyst. Alternatively, the reactor may be any type of packed reactor.

As noted above, the catalyst includes silicon carbide. The catalyst may include essentially pure silicon carbide (SiC). The catalyst may include a mixture of silicon carbide and one or more metal carbides, such as titanium carbide (TiC), zirconium carbide (ZrC), and/or chromium carbide ($Cr_3C_2$), for example. The mixture of silicon carbide and one or more metal carbides is referred to as a metal silicon carbide. The amount of silicon carbide in metal silicon carbides, as a weight percentage of the total silicon carbide and metal carbide in the catalyst, may be as little as about 50 weight percent (wt. %), about 60 wt. %, about 70 wt. %, about 80 wt. %, or about 85 wt. %, or as high as about 90 wt. %, about 95 wt. %, about 97 wt. %, about 99 wt. %, or about 99.9 wt. %, or within any range defined between any two of the foregoing values, such as about 50 wt. % to about 99.9 wt. %, about 60 wt. % to about 99 wt. %, about 70 wt. % to about 97 wt. %, about 80 wt. % to about 95 wt. %, about 85 wt. % to about 90 wt. %, about 70 wt. % to about 99.9 wt. %, or about 85 wt. % to about 99.9 wt. %, for example. Preferably, the amount of silicon carbide in the metal silicon carbide is from about 50 wt. % to about 99.9 wt. %. More preferably, the amount of silicon carbide in the metal silicon carbide is from about 70 wt. % to about 99.9 wt. %. Most preferably, the amount of silicon carbide in the metal silicon carbide is from about 85 wt. % to about 99.9 wt. %.

The catalyst may have a surface area as small as about 10 square meters per gram ($m^2/g$), about 15 $m^2/g$, about 25 $m^2/g$, about 40 $m^2/g$, about 60 $m^2/g$, or about 80 $m^2/g$, or as large as about 100 $m^2/g$, about 120 $m^2/g$, about 150 $m^2/g$, about 200 $m^2/g$, about 250 $m^2/g$, or about 300 $m^2/g$, or within any range defined between any two of the foregoing values, such as about 10 $m^2/g$ to about 300 $m^2/g$, about 15 $m^2/g$ to about 250 $m^2/g$, about 25 $m^2/g$ to about 200 $m^2/g$, about 40 $m^2/g$ to about 150 $m^2/g$, about 60 $m^2/g$ to about 120 $m^2/g$, or about 80 $m^2/g$ to about 120 $m^2/g$, for example. The surface area of the catalyst is determined by the BET method per ISO 9277:2010.

The silicon carbide or metal silicon carbide catalyst may be used alone, or may include additional metals or metal salts on the surface of the catalyst to promote catalyst activity and stability. The metals may include transition metals, such as palladium, platinum, iron and nickel. The metal salts may include any salts of alkaline metals, alkaline earth metals, transition metals, and combinations thereof. Examples of metals and metal salts may include potassium iodide, copper(I) iodide, copper(II) rubidium iodide, sodium iodide, potassium fluoride, magnesium iodide, platinum and palladium, for example. Metal salts are more preferred than metals. Preferred metal salts include potassium iodide, copper(I) iodide, and rubidium iodide.

The metal salt catalysts may be prepared by impregnating the silicon carbide or metal silicon carbide with an aqueous solution of the desired metal salt, and then drying. The metal salt catalyst may then be treated with hot nitrogen in situ before contacting the reactants.

The amount of additional metals or metal salts on the surface of the catalyst, as a percentage of the total combined weight of the silicon carbide or metal silicon carbide and the metals or metal salts may be as little as about 0.1 weight percent (wt. %), about 0.3 wt. %, about 0.5 wt. %, about 0.7 wt. %, about 1 wt. %, about 2 wt. %, or about 4 wt. % or as great as about 6 wt. %, about 8 wt. %, about 10 wt. %, about 15 wt. %, about 20 wt. %, or about 25 wt. %, or within any range defined between any two of the foregoing values, such as about 0.1 wt. % to about 25 wt. %, about 0.3 wt. % to about 20 wt. %, about 0.5 wt. % to about 15 wt. %, about 0.7 wt. % to about 10 wt. %, about 1 wt. % to about 8 wt. %, about 2 wt. % to about 6 wt. %, or about 1 wt. % to about 4 wt. %, for example. Preferably, the amount of metal salts on the surface of the catalyst is from about 1 wt. % to about 20 wt. %. More preferably, the amount of metal salts on the surface of the catalyst is from about 3 wt. % to about 15 wt. %. Most preferably, the amount of metal salts on the surface of the catalyst is from about 5 wt. % to about 10 wt. %.

The reactant stream may be in contact with the catalyst for a contact time as short as about 1 second, about 2 seconds, about 4 seconds, about 6 seconds, about 8 seconds, about 10 seconds, about 15 seconds, about 20 seconds, about 25 seconds, or about 30 seconds, or as long as about 40 seconds, about 50 seconds, about 60 seconds, about 70 seconds, about 80 seconds, about 100 seconds or about 120 seconds, or within any range defined between any two of the foregoing values, such as about 2 seconds to about 120 seconds, about 4 second to about 100 seconds, about 6 seconds to about 80 seconds, about 8 seconds to about 70 seconds, about 10 seconds to about 60 seconds, about 15 seconds to about 50 seconds, about 20 seconds to about 40 seconds, about 20 seconds to about 30 seconds, about 10 seconds to about 20 seconds, or about 100 seconds to about 120 seconds, for example. Preferably, the reactant stream is in contact with the catalyst for a contact time from about 1 second to about 100 seconds. More preferably, the reactant stream is in contact with the catalyst for a contact time from about 2 seconds to about 50 seconds. Most preferably, the reactant stream is in contact with the catalyst for a contact time from about 3 seconds to about 30 seconds.

Prior to the reaction, the catalyst may be heated to a temperature as low as about 200° C., about 250° C., about 300° C., about 325° C., about 330° C., about 340° C., about 350° C., or about 360° C., or to a temperature as high as about 370° C., about 380° C., about 390° C., about 400° C., about 450° C., about 475° C., about 500° C., about 525° C., about 550° C., about 575° C., or about 600° C., or within any range defined between any two of the foregoing values, such as about 200° C. to about 600° C., about 325° C. to about 400° C., about 330° C. to about 390° C., about 340° C. to about 380° C., about 350° C. to about 370° C., or about 340° C. to about 360° C., for example. Preferably, the catalyst is heated to a temperature from about 300° C. to about 500° C. More preferably, the catalyst is heated to a temperature from about 350° C. to about 450° C. Most preferably, the catalyst is heated to a temperature from about 375° C. to about 420° C.

Pressure is not critical. Convenient operating pressures range from about 10 kPa to about 4,000 kPa, and preferably from about 100 kPa to about 250 kPa.

As noted above, compared to activated carbon catalysts, silicon carbide catalysts are less susceptible to deactivation. However, eventually carbon deposits may accumulate on the catalyst surface and diminish catalytic activity. The silicon carbide catalysts may be regenerated by flowing oxygen gas or air thorough the reactor at temperature range from about 300° C. to about 600° C. to remove the carbon deposits. The regeneration is done when the reaction is stopped and reactants are not flowing through the reactor.

The composition of the organic compounds in the product stream exiting the reactor may be measured by gas chromatography (GC) and gas chromatography-mass spectroscopy (GC-MS) analyses. Graph areas provided by the GC analysis for each of the organic compounds may be combined to provide a GC area percentage (GC area %) of the total organic compounds for each of the organic compounds as a measurement of the relative concentrations of the organic compounds in the product stream.

The concentration of trifluoroiodomethane in the product stream exiting the reactor, in GC area % of total organic compounds, may be as low as about 10%, about 15%, about 20%, about 25%, about 30%, about 35%, about 40%, about 45%, about 50%, about 55% or about 60%, or may be as high as about 65%, about 70%, about 75%, about 80%, about 85%, about 90%, about 95%, about or 99% or within any range defined between any two of the foregoing values, such as about 10% to about 99%, about 20% to about 95%, about 30% to about 90%, about 40% to about 85%, about 45% to about 80%, about 50% to about 75%, about 55% to about 70%, about 60% to about 65%, about 90% to about 99% or about 95% to about 99%, for example. Preferably, the concentration of trifluoroiodomethane in the product stream is from about 30% to about 99%. More preferably, the concentration of trifluoroiodomethane in the product stream is from about 40% to about 99%. Most preferably, the concentration of trifluoroiodomethane in the product stream is from about 50% to about 99%.

The product stream may be directed from the reactor to an iodine removal vessel in which the product stream is cooled to allow unreacted iodine to condense to remove at least some of the iodine from the product stream to be recycled as a reactant. The product stream may be cooled to a temperature lower than the boiling point of iodine, but above the melting point of iodine, to recover the iodine in liquid form. Alternatively, or additionally, the product stream leaving the reactor may be cooled to a temperature lower than the melting point of iodine to recover the iodine in solid form. The product stream may proceed from the iodine removal vessel to one or more additional iodine removal vessels to remove additional unreacted iodine for recycle.

The product stream may then be directed from the one or more iodine removal vessels to a heavies distillation column to separate higher boiling point compounds, such as unreacted TFA, and byproducts such as pentafluoroiodoethane ($C_2F_5I$) and hydrogen fluoride (HF) from lower boiling point compounds $CF_3I$ and byproducts such as trifluoromethane ($CF_3H$), hydrogen iodide (HI), and carbon dioxide ($CO_2$). The higher boiling point compounds may be directed from a bottom stream of the heavies distillation column to a TFA recycle distillation column to separate the higher boiling point TFA from the lower boiling point byproducts $C_2F_5I$ and HF. The TFA from a bottom stream of the TFA recycle distillation column may be recycled back to the reactor. The overhead stream of the TFA recycle distillation column including the $C_2F_5I$ and HF may pass through a scrubber including a basic solution to remove the HF, and the $C_2F_5I$ may be recovered as a byproduct, or burned in a thermal oxidizer.

The overhead stream from the heavies distillation column including the $CF_3I$, $CF_3H$, HI and $CO_2$ may be directed to a $CF_3H/CO_2$ removal distillation column to separate the higher boiling point compounds $CF_3I$ and HI from the lower boiling point compounds $CF_3H$ and $CO_2$. The overhead stream of the $CF_3H/CO_2$ removal distillation column may be directed to a $CF_3H$ distillation column to separate the $CF_3H$ from the $CO_2$. The $CF_3H$ and/or the $CO_2$ may be collected as byproducts. Alternatively, the overhead stream from the $CF_3H/CO_2$ removal distillation column may be burned by a thermal oxidizer.

The bottom stream of the $CF_3H/CO_2$ removal distillation column including the $CF_3I$ and HI may be directed to a product distillation column to separate the $CF_3I$ product from the HI. The HI in the overhead stream of the product distillation column may be collected as a byproduct by passing through a water scrubber to generate an HI aqueous solution, or by compressing it to produce an anhydrous HI liquid. The $CF_3I$ may be collected from the bottom stream of the product distillation column. The recycle of the iodine and the TFA results in an efficient process for producing $CF_3I$.

The FIGURE is a process flow diagram showing an integrated process 10 for manufacturing trifluoroiodomethane. As shown in the FIGURE, the process 10 includes material flows of solid iodine 12 and liquid TFA 14. The solid iodine 12 may be continuously or intermittently added to a solid storage tank 16. A constant flow of solid iodine 18 is transferred by a solid conveying system (not shown) from the solid storage tank 16 to an iodine liquefier 20 where the solid iodine is heated to above its melting point but below its boiling point to maintain a level of liquid iodine in the iodine liquefier 20. Liquid iodine 22 flows from the iodine liquefier 20 to an iodine vaporizer 24. The iodine liquefier 20 may be pressurized by an inert gas to drive the flow of liquid iodine 22. The inert gas may include nitrogen, argon, or helium, or mixtures thereof, for example. The flow rate of the liquid iodine 22 may be controlled by a liquid flow controller 26. In the iodine vaporizer 24, the iodine is heated to above its boiling point to form a flow of iodine vapor 28.

Liquid TFA 14 may be provided to a TFA vaporizer 30, where the TFA is heated to above its boiling point to provide a flow of TFA vapor 32. The flow rate of the TFA vapor 32 may be controlled by a gas flow controller 34. The flow of iodine vapor 28 and the flow of TFA vapor 32 may be combined in a mixing valve 36 to form a reactant stream 38. The reactant stream 38 may be provided to a reactor 40.

The reactant stream 38 may react in the presence of a catalyst 42 contained within the reactor 40 to produce a product stream 44. The catalyst 42 may be any of the catalysts described herein. The product stream 44 may include trifluoroiodomethane, unreacted iodine, unreacted TFA, and reaction by-products such as HI, $CO_2$, $CF_3H$, HF, and $C_2F_5I$, for example.

The product stream 44 may be provided to an upstream valve 46. The upstream valve 46 may direct the product stream 44 to an iodine removal step. In this step, a first iodine removal train 48a may include a first iodine removal vessel 50a and a second iodine removal vessel 50b. The product stream 44 may be cooled in the first iodine removal vessel 50a to a temperature below the boiling point of the iodine to condense at least some of the iodine, separating it from the product stream 44. The product stream 44 may be further cooled in the first iodine removal vessel 50a to a temperature below the melting point of the iodine to separate even more iodine from the product stream 44, depositing at least some of the iodine within the first iodine removal vessel 50a as a solid and producing a reduced iodine product stream 52. The reduced iodine product stream 52 may be provided to the second iodine removal vessel 50b and cooled to separate at least some more of the iodine from the reduced iodine product stream 52 to produce an iodine-free product stream 54. The iodine-free product stream 54 may be provided to a heavies distillation column 60.

Although the first iodine removal train 48a consists of two iodine removal vessels operating in a series configuration, it is understood that the first iodine removal train 48a may include two or more iodine removal vessels operation in a parallel configuration, more than two iodine removal vessels operating in a series configuration, and any combination thereof. It is also understood that the first iodine removal train 48a may consist of a single iodine removal vessel.

The iodine collected in the first iodine removal vessel 50a may form a first iodine recycle stream 56a. Similarly, the iodine collected in the second iodine removal vessel 50b may form a second iodine recycle stream 56b. Each of the first iodine recycle stream 56a and the second iodine recycle stream 56b may be provided to the iodine liquefier 20. Should the iodine be collected in liquid form, the liquid iodine may be provided to the iodine liquefier 20 continuously. However, it may be preferred to collect the iodine in solid form because the lower temperature will result in more effective removal of the iodine from the product stream 44 and the reduced iodine product stream 52.

In order to provide continuous operation while collecting the iodine in solid form, the upstream valve 46 may be configured to selectively direct the product stream 44 to a second iodine removal train 48b. The second iodine removal train 48b may be substantially as described above for the first iodine removal train 48a. Once either the first iodine removal vessel 50a or the second iodine removal vessel 50b of the first iodine removal train 48a accumulates enough solid iodine that it is beneficial to remove it, the upstream valve 46 may be selected to direct the product stream 44 from the first iodine removal train 48a to the second iodine removal train 48b. At about the same time, a downstream valve 58 configured to selectively direct the iodine-free product stream 54 from either of the first iodine removal train 48a or the second iodine removal train 48b to the heavies distillation column 60 may be selected to direct the iodine-free product stream 54 from the second iodine removal train 48b to the heavies distillation column 60 so that the process of removing the iodine from the product stream 44 to produce the iodine-free product stream 54 may continue uninterrupted. Once the product stream 44 is no longer directed to the first iodine removal train 48a, the first iodine removal vessel 50a and the second iodine removal vessel 50b of the first iodine removal train 48a may be heated to above the melting point of the iodine, liquefying the solid iodine so that it may flow through the first iodine recycle stream 56a and the second iodine recycle stream 56b of the first iodine removal train 48a to the iodine liquefier 20.

As the process continues and either of the first iodine removal vessel 50a or the second iodine removal vessel 50b of the second iodine removal train 48b accumulates enough solid iodine that it is beneficial to remove it, the upstream valve 46 may be selected to direct the product stream 44 from the second iodine removal train 48b back to the first iodine removal train 48a, and the downstream valve 58 may be selected to direct the iodine product stream 54 from the first iodine removal train 48a to the heavies distillation column 60 so that the process of removing the iodine from the product stream 44 to produce the iodine-free product stream 54 may continue uninterrupted. Once the product stream 44 is no longer directed to the second iodine removal train 48b, the first iodine removal vessel 50a and the second iodine removal vessel 50b of the second iodine removal train 48b may be heated to above the melting point of the iodine, liquefying the solid iodine so that it may flow through the first iodine recycle stream 56a and the second iodine recycle stream 56b of the second iodine removal train 48b to the iodine liquefier 20. By continuing to switch between the first iodine removal train 48a and the second iodine removal train 48b, the unreacted iodine in the product stream 44 may be efficiently and continuously removed and recycled.

As described above, the liquid iodine may flow through the first iodine recycle streams 56a and the second iodine recycle streams 56b of the first iodine removal train 48a and the second iodine removal train 48b to the iodine liquefier 20. Alternatively, the liquid iodine may flow through the first iodine recycle streams 56a and the second iodine recycle streams 56b of the first iodine removal train 48a and the second iodine removal train 48b to the iodine vaporizer 24, bypassing the iodine liquefier 20 and the liquid flow controller 26.

The heavies distillation column 60 may be configured for the separation of organic heavies, such as unreacted TFA, and byproducts $C_2F_5I$ and HF from organic lights, such as $CF_3I$ and byproducts $CF_3H$, HI and $CO_2$. A bottom stream 62 including the organic heavies from the heavies distillation column 60 may be provided to a TFA recycle column 64. The TFA recycle column 64 may be configured for the separation of the unreacted TFA from the byproducts $C_2F_5I$ and HF. A bottom stream 66 of the TFA recycle column 64 including the unreacted TFA may be recycled back to the reactor 40. Alternatively, the bottom stream 66 of the TFA recycle column 64 including the unreacted TFA may be recycled back to the TFA vaporizer 30. An overhead stream 68 of the TFA recycle column 64 including the byproducts $C_2F_5I$ and HF may be treated by a caustic solution (not shown) to remove the HF and the $C_2F_5I$ may be burned in a thermal oxidizer (not shown).

An overhead stream 70 including the organic lights from the heavies distillation column 60 may be provided to a $CF_3H/CO_2$ removal column 72. The $CF_3H/CO_2$ removal column 72 may be configured for the separation of the byproducts $CF_3H$ and $CO_2$ from the $CF_3I$ and the byproduct HI. An overhead stream 74 of the $CF_3H/CO_2$ removal column 72 including the byproducts $CF_3H$ and $CO_2$ may be provided to a $CF_3H$ column 76. The $CF_3H$ column 76 may be configured to separate the $CF_3H$ from the $CO_2$. A bottom stream 78 of the $CF_3H$ column 76 including the $CO_2$ may be recovered as a byproduct. An overhead stream 80 of the $CF_3H$ column including the $CF_3H$ may be recovered as a byproduct. Alternatively, the overhead stream 74 of the $CF_3H/CO_2$ removal column 72 including the byproducts $CF_3H$ and $CO_2$ may bypass the $CF_3H$ column 76 and be burned in a thermal oxidizer (not shown).

A bottom stream 82 including the $CF_3I$ and the byproduct HI from the $CF_3H/CO_2$ removal column 72 may be provided to a product column 84. The product column 84 may be configured to separate the $CF_3I$ from the HI. An overhead stream 86 of the product column 84 including the HI may be compressed into liquid HI, or treated by a water scrubber (not shown) to produce an HI solution. The liquid HI or HI solution may be converted back to iodine and recycled by any means commercially available. The resulting product $CF_3I$ may be collected from a bottom stream 88 of the product column 84.

While this invention has been described as relative to exemplary designs, the present invention may be further modified within the spirit and scope of this disclosure. Further, this application is intended to cover such departures from the present disclosure as come within known or customary practice in the art to which this invention pertains.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

EXAMPLES

Evaluation of SiC-Based Catalysts in the Manufacture of $CF_3I$

In the following Examples, the manufacture of trifluoroiodomethane from TFA and iodine according to Equation 1 described above was demonstrated for a variety of SiC-based catalysts. Vaporized TFA from a TFA vaporizer was fed into an iodine vaporizer at a measured feed rate. The iodine vaporizer was initially charged with 1,000 g of solid iodine. The temperature of the iodine vaporizer was maintained at 150° C. to 165° C. to generate an iodine vapor which mixed with the TFA vapor. The mixture of iodine vapor and TFA vapor was fed to a fixed bed tubular reactor which was loaded with a specific SiC-based catalyst preheated to a predetermined reaction temperature. The reaction was carried out at atmospheric pressure. The reactor effluent was passed through two iodine removal vessels in series to collect unreacted iodine in solid form, and then fed to a deionized water scrubber to capture unreacted TFA.

Periodically, samples were taken from the effluent of the deionized water scrubber and the composition of the organic compounds in the samples were measured by gas chromatography (GC). Graph areas provided by the GC analysis for each of the organic compounds were combined to provide a GC area percentage (GC area %) of the total organic compounds for each of the organic compounds as a measurement of the relative concentrations of the organic compounds in the samples to determine the mol. % selectivity in the production of the $CF_3I$. At the end of the run time of the reaction, the system was shut down and the weight loss of the iodine vaporizer and the weight gain of the iodine removal vessels were measured to determine a feed ratio of moles of iodine to moles of TFA. A residence time in the reactor was calculated based on the combined feed rates of the iodine and the TFA.

The results for each example are shown in Table 1. For each Example, Table 1 shows the catalyst used, the BET surface area, the catalyst preheat temperature, the feed rate of the TFA, the reaction run time, the molar feed ratio of I2 to TFA, the residence time, and the mol. % selectivity in the production of $CF_3I$ at the end of the run.

TABLE 1

| Example | 1 | 2 | 3 | 4 | 5 | 6 | 7 | 8 | 9 |
|---|---|---|---|---|---|---|---|---|---|
| Catalyst | SiC | TiC-SiC | TiC-SiC | SiC | SiC | SiC + CuI | SiC + KI | SiC + RbI | SiC + Pd |
| Catalyst Loading (wt. %) | 0 | 0 | 0 | 0 | 0 | 5 | 5 | 5 | 1 |
| Surface Area (m$^2$/g) | 18 | 18 | 18 | 30 | 30 | 18 | 18 | 18 | 18 |
| Preheat Temp. (° C.) | 400 | 350 | 400 | 350 | 400 | 400 | 400 | 400 | 400 |
| TFA Feed Rate (g/hr.) | 9.2 | 8.0 | 7.7 | 8.0 | 8.2 | 8.3 | 8.0 | 8.9 | 8.9 |
| Run Time (hrs.) | 18 | 24 | 22 | 9 | 18 | 38 | 48 | 16 | 26 |
| Molar Feed Ratio (I$_2$/TFA) | 1.14 | 1.18 | 1.16 | 1.19 | 1.03 | 0.98 | 0.97 | 0.94 | 1.08 |
| Residence Time (sec.) | 4.2 | 5.1 | 5.0 | 5.1 | 5.0 | 5.0 | 5.2 | 4.8 | 4.5 |
| CF$_3$I Selectivity (mol. %) | 43.3 | 59.1 | 58.9 | 28.5 | 48.7 | 50.6 | 47.3 | 65.9 | 46.8 |

Aspects

Aspect 1 is a process for producing trifluoroiodomethane (CF$_3$I). The process includes providing a vapor-phase reactant stream comprising trifluoroacetic acid and iodine, and reacting the reactant stream in the presence of a catalyst to produce a product stream comprising the trifluoroiodomethane. The catalyst includes silicon carbide.

Aspect 2 is the process of Aspect 1, wherein in the providing step, the trifluoroacetic acid comprises less than about 1,000 ppm by volume of water.

Aspect 3 is the process of Aspect 1, wherein in the providing step, the trifluoroacetic acid comprises less than about 100 ppm by volume of water.

Aspect 4 is the process of Aspect 1, wherein in the providing step, the trifluoroacetic acid comprises less than about 30 ppm by volume of water.

Aspect 5 is the process of Aspect 1, wherein in the providing step, the trifluoroacetic acid comprises less than about 10 ppm by volume of water.

Aspect 6 is the process of any of Aspects 1-5, wherein in the providing step, the iodine comprises less than about 500 ppm by volume of water.

Aspect 7 is the process of any of Aspects 1-5, wherein in the providing step, the iodine comprises less than about 100 ppm by volume of water.

Aspect 8 is the process of any of Aspects 1-5, wherein in the providing step, the iodine comprises less than about 30 ppm by volume of water.

Aspect 9 is the process of any of Aspects 1-5, wherein in the providing step, the iodine comprises less than about 10 ppm by volume of water.

Aspect 10 is the process of any of Aspects 1-9, wherein in the providing step, a mole ratio of the trifluoroacetic acid to the iodine is from about 0.1:1 to about 5:1.

Aspect 11 is the process of any of Aspects 1-9, wherein in the providing step, a mole ratio of the trifluoroacetic acid to the iodine is from about 0.8:1 to about 1.5:1.

Aspect 12 is the process of any of Aspects 1-9, wherein in the providing step, a mole ratio of the trifluoroacetic acid to the iodine is from about 1:1 to about 1.2:1.

Aspect 13 is the process of any of Aspects 1-9, wherein in the providing step, a mole ratio of the trifluoroacetic acid to the iodine is from about 1:1 to about 1.1:1.

Aspect 14 is the process of any of Aspects 1-13, wherein the catalyst further comprises a metal carbide.

Aspect 15 is the process of Aspect 14, wherein the metal carbide includes at least one selected from a group of titanium carbide, zirconium carbide, and chromium carbide.

Aspect 16 is the process of Aspect 15, wherein the metal carbide includes titanium carbide.

Aspect 17 is the process of Aspect 15, wherein the metal carbide consists essentially of titanium carbide.

Aspect 18 is the process of Aspect 15, wherein the metal carbide consists of titanium carbide.

Aspect 19 is the process of Aspect 15, wherein the metal carbide includes zirconium carbide.

Aspect 20 is the process of Aspect 15, wherein the metal carbide consists essentially of zirconium carbide.

Aspect 21 is the process of Aspect 15, wherein the metal carbide consists of zirconium carbide.

Aspect 22 is the process of Aspect 15, wherein the metal carbide includes chromium carbide.

Aspect 23 is the process of Aspect 15, wherein the metal carbide consists essentially of chromium carbide.

Aspect 24 is the process of Aspect 15, wherein the metal carbide consists of chromium carbide.

Aspect 25 is the process of any of Aspects 14-24, wherein an amount of silicon carbide in the catalyst, as a weight percentage of the total silicon carbide and metal carbide in the catalyst is from about 50 wt. % to about 99.9 wt. %.

Aspect 26 is the process of any of Aspects 14-24, wherein an amount of silicon carbide in the catalyst, as a weight percentage of the total silicon carbide and metal carbide in the catalyst is from about 70 wt. % to about 99.9 wt. %.

Aspect 27 is the process of any of Aspects 14-24, wherein an amount of silicon carbide in the catalyst, as a weight percentage of the total silicon carbide and metal carbide in the catalyst is from about 85 wt. % to about 99.9 wt. %.

Aspect 28 is the process of any of Aspects 1-27, wherein the catalyst further comprises at least one selected from the group of a metal and a metal salt deposited on a surface of the catalyst.

Aspect 29 is the process of Aspect 28, wherein the catalyst comprises a metal salt, the metal sale including at least one selected from the group of potassium iodide, copper(I) iodide, copper(II) rubidium iodide, sodium iodide, potassium fluoride, magnesium iodide, platinum and palladium.

Aspect 30 is the process of Aspect 29, wherein the metal salt includes potassium iodide.

Aspect 31 is the process of Aspect 29, wherein the metal salt consists essentially of potassium iodide.

Aspect 32 is the process of Aspect 29, wherein the metal salt consists of potassium iodide.

Aspect 33 is the process of Aspect 29, wherein the metal salt includes copper(I) iodide.

Aspect 34 is the process of Aspect 29, wherein the metal salt consists essentially of copper(I) iodide.

Aspect 35 is the process of Aspect 29, wherein the metal salt consists of copper(I) iodide.

Aspect 36 is the process of Aspect 29, wherein the metal salt includes rubidium iodide.

Aspect 37 is the process of Aspect 29, wherein the metal salt consists essentially of rubidium iodide.

Aspect 38 is the process of Aspect 29, wherein the metal salt consists of rubidium iodide.

Aspect 39 is the process of any of Aspects 28-38, wherein the metals or metal salts on the surface of the catalyst, as a percentage of the total combined weight of the silicon carbide or metal silicon carbide and the metals or metal salts is from 0.1 wt. % to about 25 wt. %.

Aspect 40 is the process of any of Aspects 28-38, wherein the metals or metal salts on the surface of the catalyst, as a percentage of the total combined weight of the silicon carbide or metal silicon carbide and the metals or metal salts is from about 1 wt. % to about 20 wt. %.

Aspect 41 is the process of any of Aspects 28-38, wherein the metals or metal salts on the surface of the catalyst, as a percentage of the total combined weight of the silicon carbide or metal silicon carbide and the metals or metal salts is from about 3 wt. % to about 15 wt. %.

Aspect 42 is the process of any of Aspects 28-38, wherein the metals or metal salts on the surface of the catalyst, as a percentage of the total combined weight of the silicon carbide or metal silicon carbide and the metals or metal salts is from about 5 wt. % to about 10 wt. %.

Aspect 43 is the process of any of Aspects 1-42, wherein a contact time of the reactant stream with the catalyst is from about 1 second to about 120 seconds.

Aspect 44 is the process of any of Aspects 1-42, wherein a contact time of the reactant stream with the catalyst is from about 1 second to about 100 seconds.

Aspect 45 is the process of any of Aspects 1-42, wherein a contact time of the reactant stream with the catalyst is from about 2 seconds to about 50 seconds.

Aspect 46 is the process of any of Aspects 1-42, wherein a contact time of the reactant stream with the catalyst is from about 3 seconds to about 30 seconds.

Aspect 47 is the process of any of Aspects 1-46, further comprising heating the catalyst to a temperature from about 200° C. to about 600° C. before the reacting step.

Aspect 48 is the process of any of Aspects 1-46, further comprising heating the catalyst to a temperature from about 300° C. to about 500° C. before the reacting step.

Aspect 49 is the process of any of Aspects 1-46, further comprising heating the catalyst to a temperature from about 350° C. to about 450° C. before the reacting step.

Aspect 50 is the process of any of Aspects 1-46, further comprising heating the catalyst to a temperature from about 375° C. to about 425° C. before the reacting step.

Aspect 51 is the process of any of Aspects 1-50, wherein the product stream further comprises unreacted iodine and the process further comprises the additional steps of separating the unreacted iodine from the product stream as solid iodine, heating the solid iodine to produce liquid iodine, and returning the liquid iodine to the reactant stream.

Aspect 52 is the process of any of Aspects 1-51, wherein the process is a continuous process.

Aspect 53 is the process of any of Aspects 1-51, wherein the process is a batch process.

Aspect 54 is the process of any of Aspects 1-53, wherein the product stream further comprises unreacted trifluoroacetic acid and the process further comprises the additional steps of separating the trifluoroacetic acid from the product stream and returning the separated trifluoroacetic acid to the reactant stream.

Aspect 55 a process for producing trifluoroiodomethane (CF$_3$I), the process including the steps of reacting trifluoroacetic acid and iodine in the vapor phase in the presence of a catalyst to produce a product stream comprising the trifluoroiodomethane and unreacted iodine, the catalyst comprising silicon carbide; removing at least some of the unreacted iodine from the product stream by cooling the product stream to form solid iodine, the solid iodine forming in a first iodine removal vessel and/or a second iodine removal vessel; producing liquid iodine from the solid iodine by heating the first iodine removal vessel to liquefy the solid iodine when cooling the product stream through the second iodine removal vessel or heating the second iodine removal vessel to liquefy the solid iodine when cooling the product stream through the first iodine removal vessel, and recycling the liquified iodine to the reacting step.

Aspect 56 is the process of Aspect 55 product stream further comprises unreacted trifluoroacetic acid and the process further comprises the additional steps of separating the trifluoroacetic acid from the product stream and recycling the separated trifluoroacetic acid to the reacting step.

Aspect 57 is the process of either of Aspects 55 or 56, wherein the process is a continuous process.

Aspect 58 is the process of either of Aspects 55 or 56, wherein the catalyst further comprises a metal carbide.

Aspect 59 is the process of Aspect 58, wherein the metal carbide includes at least one selected from a group of titanium carbide, zirconium carbide, and chromium carbide.

Aspect 60 is the process of Aspect 59, wherein the metal carbide includes titanium carbide.

Aspect 61 is the process of Aspect 59, wherein the metal carbide consists essentially of titanium carbide.

Aspect 62 is the process of Aspect 59, wherein the metal carbide consists of titanium carbide.

Aspect 63 is the process of Aspect 59, wherein the metal carbide includes zirconium carbide.

Aspect 64 is the process of Aspect 59, wherein the metal carbide consists essentially of zirconium carbide.

Aspect 65 is the process of Aspect 59, wherein the metal carbide consists of zirconium carbide.

Aspect 66 is the process of Aspect 59, wherein the metal carbide includes chromium carbide.

Aspect 67 is the process of Aspect 59, wherein the metal carbide consists essentially of chromium carbide.

Aspect 68 is the process of Aspect 59, wherein the metal carbide consists of chromium carbide.

Aspect 69 is the process of any of Aspects 58-68, wherein an amount of silicon carbide in the catalyst, as a weight percentage of the total silicon carbide and metal carbide in the catalyst is from about 50 wt. % to about 99.9 wt. %.

Aspect 70 is the process of any of Aspects 58-68, wherein an amount of silicon carbide in the catalyst, as a weight percentage of the total silicon carbide and metal carbide in the catalyst is from about 70 wt. % to about 99.9 wt. %.

Aspect 71 is the process of any of Aspects 58-68, wherein an amount of silicon carbide in the catalyst, as a weight percentage of the total silicon carbide and metal carbide in the catalyst is from about 85 wt. % to about 99.9 wt. %.

Aspect 72 is the process of any of Aspects 55-71, wherein the catalyst further comprises at least one selected from the group of a metal and a metal salt deposited on a surface of the catalyst.

Aspect 73 is the process of Aspect 72, wherein the catalyst comprises a metal salt, the metal sale including at least one selected from the group of potassium iodide, copper(I) iodide, copper(II) rubidium iodide, sodium iodide, potassium fluoride, magnesium iodide, platinum and palladium.

Aspect 74 is the process of Aspect 73, wherein the metal salt includes potassium iodide.

Aspect 75 is the process of Aspect 73, wherein the metal salt consists essentially of potassium iodide.

Aspect 76 is the process of Aspect 73, wherein the metal salt consists of potassium iodide.

Aspect 77 is the process of Aspect 73, wherein the metal salt includes copper(I) iodide.

Aspect 78 is the process of Aspect 73, wherein the metal salt consists essentially of copper(I) iodide.

Aspect 79 is the process of Aspect 73, wherein the metal salt consists of copper(I) iodide.

Aspect 80 is the process of Aspect 73, wherein the metal salt includes rubidium iodide.

Aspect 81 is the process of Aspect 73, wherein the metal salt consists essentially of rubidium iodide.

Aspect 82 is the process of Aspect 73, wherein the metal salt consists of rubidium iodide.

Aspect 83 is the process of any of Aspects 72-82, wherein the metals or metal salts on the surface of the catalyst, as a percentage of the total combined weight of the silicon carbide or metal silicon carbide and the metals or metal salts is from 0.1 wt. % to about 25 wt. %.

Aspect 84 is the process of any of Aspects 72-82, wherein the metals or metal salts on the surface of the catalyst, as a percentage of the total combined weight of the silicon carbide or metal silicon carbide and the metals or metal salts is from about 1 wt. % to about 20 wt. %.

Aspect 85 is the process of any of Aspects 72-82, wherein the metals or metal salts on the surface of the catalyst, as a percentage of the total combined weight of the silicon carbide or metal silicon carbide and the metals or metal salts is from about 3 wt. % to about 15 wt. %.

Aspect 86 is the process of any of Aspects 72-82, wherein the metals or metal salts on the surface of the catalyst, as a percentage of the total combined weight of the silicon carbide or metal silicon carbide and the metals or metal salts is from about 5 wt. % to about 10 wt. %.

What is claimed is:

1. A process for producing trifluoroiodomethane ($CF_3I$), the process comprising:
   providing a vapor-phase reactant stream comprising trifluoroacetic acid and iodine; and
   reacting the reactant stream in the presence of a catalyst to produce a product stream comprising the trifluoroiodomethane, the catalyst comprising silicon carbide.

2. The process of claim 1, wherein in the providing step, the trifluoroacetic acid comprises less than about 500 ppm by volume of water.

3. The process of claim 1, wherein in the providing step, the iodine comprises less than about 500 ppm by weight of water.

4. The process of claim 1, wherein in the providing step, a mole ratio of the iodine to the trifluoroacetic acid is from about 0.1:1 to about 2:1.

5. The process of claim 1, wherein the catalyst further comprises a metal carbide.

6. The process of claim 5, wherein the metal carbide is titanium carbide.

7. The process of claim 1, wherein the catalyst further comprises at least one selected from the group of a metal and a metal salt deposited on a surface of the catalyst.

8. The process of claim 7, wherein the metal or metal salt is from about 0.1 wt. % to about 25 wt. % of the total weight of the catalyst.

9. The process of claim 7, wherein the metal salt comprises at least one selected from the group of potassium iodide, copper iodide, and rubidium iodide.

10. The process of claim 1, wherein in the reacting step, a contact time of the reactant stream with the catalyst is from about 1 second to about 120 seconds.

11. The process of claim 1, further comprising heating the catalyst to a temperature from about 200° C. to about 600° C. before the reacting step.

12. The process of claim 1, wherein the product stream further comprises unreacted iodine and the process further comprises the additional steps of:
   separating the unreacted iodine from the product stream as solid iodine;
   heating the solid iodine to produce liquid iodine; and
   returning the liquid iodine to the reactant stream.

13. The process of claim 11, wherein the process is a continuous process.

14. The process of claim 11, wherein the product stream further comprises unreacted trifluoroacetic acid and the process further comprises the additional steps of:
   separating the trifluoroacetic acid from the product stream; and
   returning the separated trifluoroacetic acid to the reactant stream.

15. A process for producing trifluoroiodomethane ($CF_3I$), the process comprising the following steps:
   reacting trifluoroacetic acid and iodine in the vapor phase in the presence of a catalyst to produce a product stream comprising the trifluoroiodomethane and unreacted iodine, the catalyst comprising silicon carbide;
   removing at least some of the unreacted iodine from the product stream by cooling the product stream to form solid iodine, the solid iodine forming in one of:
   a first iodine removal vessel; or
   a second iodine removal vessel;
   producing liquid iodine from the solid iodine by:
   heating the first iodine removal vessel to liquefy the solid iodine when cooling the product stream through the second iodine removal vessel; or
   heating the second iodine removal vessel to liquefy the solid iodine when cooling the product stream through the first iodine removal vessel; and
   recycling the liquified iodine to the reacting step.

16. The process of claim 15, wherein the product stream further comprises unreacted trifluoroacetic acid and the process further comprises the additional steps of:
   separating the trifluoroacetic acid from the product stream; and
   recycling the separated trifluoroacetic acid to the reacting step.

17. The process of claim 15, wherein the process is a continuous process.

18. The process of claim 15, wherein the catalyst further comprises a metal carbide.

19. The process of claim 15, wherein the catalyst further comprises at least one selected from the group of a metal and a metal salt deposited on a surface of the catalyst.

20. The process of claim 19, wherein catalyst comprises a metal salt comprising at least one selected from the group of potassium iodide, copper iodide, and rubidium iodide.

* * * * *